United States Patent [19]

Schneider et al.

[11] 4,424,394

[45] Jan. 3, 1984

[54] MANUFACTURE OF ARYLACETIC ACIDS AND THEIR ESTERS

[75] Inventors: Kurt Schneider, Bad Durkheim; Rudolf Kummer, Frankenthal; Kurt Schwirten, Ludwigshafen, all of Fed. Rep. of Germany; Hans-Dieter Schindler, deceased, late of Frankenthal, Fed. Rep. of Germany; Maria E. Schindler, heir-at-law; Ute Lang, heir-at-law, Neuried, both of Fed. Rep. of Germany; Rainer Schindler, heir-at-law, Hechendorf, Fed. Rep. of Germany

[73] Assignee: BASF Aktiengesellschaft, Fed. Rep. of Germany

[21] Appl. No.: 92,444

[22] Filed: Nov. 8, 1979

Related U.S. Application Data

[63] Continuation of Ser. No. 676,572, Apr. 13, 1976, abandoned.

[30] Foreign Application Priority Data

May 15, 1975 [DE] Fed. Rep. of Germany ....... 2521601

[51] Int. Cl.[3] ...................... C07C 67/36; C07C 69/76; C07C 179/10; C07C 51/00

[52] U.S. Cl. ...................................... 560/105; 560/20; 560/21; 560/22; 560/23; 560/55; 560/59; 560/61; 560/62; 560/81; 560/83; 560/97; 560/100; 560/102; 560/104; 562/406; 546/174; 546/341; 549/66

[58] Field of Search ...................... 562/406; 560/20, 21, 560/22, 23, 55, 59, 61, 62, 81, 83, 97, 100, 102, 104, 105; 260/465 R; 546/341, 174; 549/66

[56] References Cited

U.S. PATENT DOCUMENTS

| | | | |
|---|---|---|---|
| 2,865,707 | 12/1958 | Hogsed | 23/50 |
| 3,116,306 | 12/1963 | Heck et al. | 260/410.9 |
| 3,974,202 | 8/1976 | Elchahawi et al. | 260/476 R |

OTHER PUBLICATIONS

Falbe–Carbon Monoxide in Organic Synthesis, Springer–Verlag, New York, Heidelberg, Ger. (1970), pp. 118–120.

*Primary Examiner*—Frederick E. Waddell
*Attorney, Agent, or Firm*—Keil & Witherspoon

[57] ABSTRACT

Arylacetic acids and their esters, of the formula $Ar(CH_2\text{-}COOR)_n$ (where Ar=aryl, R is H or a hydrocarbon radical, and n is 1 or 2) are manufactured by carbonylation of halomethylaryl compounds $Ar(CH_2C)_n$ (where X is Cl, Br or I) with carbon monoxide and a catalyst $m^+$ $[Fe(O)_3NO]^-$ (where M is an alkali metal, ammonium or one equivalent of an alkaline earth metal) in the presence of stoichiometric amounts of an inorganic base or of an alcoholate of an alcohol ROH.

11 Claims, No Drawings

MANUFACTURE OF ARYLACETIC ACIDS AND THEIR ESTERS

This is a continuation of application Ser. No. 676,572, filed Apr. 13, 1976, which application has now been abandoned.

The present invention relates to a new process for the manufacture of arylacetic acids and their esters, of the general formula I $$Ar(CH_2{-}COOR)_n \qquad I$$

where Ar is aryl and R is hydrogen or a hydrocarbon radical, and n is 1 or 2.

The manufacture of such compounds by carbonylation of halomethylaryl compounds of the general formula II $$Ar(CH_2X)_n \qquad II$$

where X is chlorine, bromine or iodine, in the presence of iron carbonyls or cobalt carbonyls as catalysts, has been disclosed. However, cobalt is relatively expensive and therefore requires continual, and technically rather involved, regeneration, whilst when using iron carbonyls the yields are totally unsatisfactory.

Further, J. Chem. Soc. 1967, page 2,255 et seq. discloses reacting benzyl chloride with equimolar amounts of triphenylphosphine and the complex compound $$Na^+[Fe(CO)_3NO]^-$$

and thereafter with sodium methylate, to give the methyl ester of phenylacetic acid. Since this is a stoichiometric reaction, the process is highly uneconomical.

It is an object of the present invention to provide a more economical method of obtaining the compounds I.

We have found that this object is achieved and that arylacetic acids, and their esters, of the general formula I $$Ar(CH_2{-}COOR)_n \qquad I$$

where Ar is aryl, R is hydrogen or a hydrocarbon radical, and n is 1 or 2, are obtained by carbonylation of halomethylaryl compounds of the general formula II $$Ar(CH_2X)_n \qquad II$$

where X is chlorine, bromine or iodine, with carbon monoxide and an iron carbonyl compound as the catalyst and with stoichiometric amounts of an inorganic base of of an alcoholate of an alcohol ROH, if the iron carbonyl compound used is a compound of the general formula III $$M^+[Fe(CO)_3NO]^- \qquad III$$

where M is an alkali metal cation or ammonium cation or one equivalent of an alkaline earth metal cation.

The iron carbonyl compounds III, the use of which is essential to the invention, are readily obtainable by conventional methods, e.g. by the process of U.S. Pat. No. 2,865,707, from iron pentacarbonyl and a nitrite $MNO_2$.

Amongst the compounds III, the sodium salt is preferred as being the cheapest. The potassium, ammonium, calcium and magnesium salt are also suitable, but for economic reasons the other alkali metal salts and alkaline earth metal salts are less suitable.

On average, from about 0.01 to 0.2 mole of the catalyst III is required to produce 1 mole of I. It is advisable to carry out the reaction in such a way that from 0.001 to 1 mole, preferably from 0.02 to 0.2 mole, of the catalyst is always available per mole of II. In the high catalyst concentration range, the reaction can be carried out at relatively low carbon monoxide pressure, e.g. from about 1 to 10 bars, and low temperatures, e.g. from about 20° to 80° C., whilst in the lower catalyst concentration range, higher pressures, e.g. from about 5 to 100 bars, and higher temperatures, e.g. from about 20° to 120° C., are advisable. However, all these values are non-critical and primarily only influence the rate of reaction, in accordance with known laws.

A general category of suitable starting compounds II are the monohalomethyl derivatives and dihalomethyl derivatives of aromatic hydrocarbons. For economic reasons, the chlorine compounds are as a rule to be preferred, though the bromine compounds and iodine compounds are more reactive and therefore at times more suitable.

The halomethyl groups are in each case present on the nucleus of the aromatic hydrocarbon $ArH_n$, from which the particular starting compound is derived.

Amongst the compounds II, benzyl chloride is the most important, since it can be used for the preparation of phenylacetic acid, which is important as an intermediate for the manufacture of phenylethanol and benzyl ketones, and the phenylacetic acid ester category of scents. A further group of important starting compounds II are those of the general formula IIa

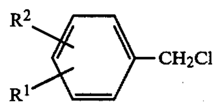

IIa where $R^1$ is alkyl of 1 to 12 carbon atoms, vinyl, alkoxy of 1 to 4 carbon atoms, chlorine, phenyl (which may in turn be substituted) or cyano, and $R^2$ is hydrogen or has one of the meanings of $R^1$. The corresponding compounds derived from polynuclear aromatic hydrocarbons, e.g. 1-methyl-2-chloromethyl-naphthalene, can also be used.

Finally, aryl also includes heterocyclic rings such as the pyridine radical, the quinoline radicals or the thiophene radical. These heterocyclic radicals may also carry the substituents $R^1$ and $R^2$.

If n is 2, as, e.g., in the case of p-xylylene chloride, a double carbonylation takes place and the corresponding dicarboxylic acids and their esters are obtained; these are mainly of importance for the manufacture of polyesters and polyamides. The starting compounds of this series may again carry further substituents $R^1$ and $R^2$.

According to our observation to date, the success of the carbonylation reaction according to the invention is virtually independent of the nature of the starting compounds II as defined above, since it is above all the presence of the $Ar{-}CH_2{-}X$ group which is important.

The intermediate complexes of the $Ar{-}CH_2{-}CO{-}Fe(CO)_2NO$ type, formed during the reaction, are converted by means of the inorganic bases or alcoholates into the acids or esters $Ar{-}CH_2{-}CO{-}OR$, by which reaction the catalyst is substantially regenerated at the same time. The amount of base used should be very close to the stoichiometric amount. If less base is used, the reaction remains incomplete whilst if more base is used, salts of the acids I are formed.

Examples of suitable bases to use for the manufacture of the acids I are the hydroxides, oxides, or salts of weak acids, such as the carbonates, of alkali metals or, preferably, of alkaline earth metals. Calcium oxide and calcium hydroxide are industrially of great importance in this context. To manufacture the esters I, the alkaline earth metal alcoholates or, preferably, the alkali metal alcoholates of the alcohols ROH are used, the sodium alcoholates being of greatest importance.

Hydrocarbon radicals R are, above all, methyl and ethyl, but also, more generally, alkyl and alkenyl of up to 18 carbon atoms. R may also, e.g., be phenyl.

Of course, the acids I are also obtainable by conventional methods via the esters I, and vice versa.

The reaction is preferably carried out in the presence of from 50 to 500% by weight, based on the amount of II, of a solvent. Suitable solvents are ethers, dioxane, tetrahydrofuran, dimethylformamide, dimethylsulfoxide and, above all, alcohols ROH. Small amounts of water are as a rule not objectionable.

Apart from the use, according to the invention, of the catalysts III, the reaction is carried out in the conventional manner, i.e. at from 20° to 120° C. under a carbon monoxide pressure of from 1 to 100 bars. If solid salts precipitate during the reaction, the reaction is preferably carried out batchwise, but can also be adapted to continuous operation.

After completion of the reaction, it is convenient to convert the catalyst to iron oxide by passing air into the reaction mixture and then to work up the latter in the conventional manner to give the desired products.

The products I are agents and/or valuable intermediates for organic syntheses. The lower alkyl esters of the phenylacetic acids, which are known scents used extensively in detergents, cleansing agents, polishes and cosmetic preparations, deserve particular mention. Phenylacetic acid esters are also starting materials for phenylethanol, which is an important scent.

EXAMPLE 1

110 g (0.87 mole) of benzyl chloride and, simultaneously but separately, a solution of 46 g (0.85 mole) of sodium methylate in 130 g of methanol, were added gradually in the course of one hour, with vigorous stirring, to a solution of 160 g of methanol and 10 g of $K[Fe(CO)_3NO]$ (0.048 mole) under a carbon monoxide pressure of 1.7 bars, at 55° C. The reaction was complete after a further two hours. Conventional working up gave methyl phenylacetate in 85% yield.

EXAMPLE 2

A suspension of 66 g (1.18 moles) of calcium oxide in 90 g of water was first added to a solution of 21 g (0.1 mole) of $K[Fe(CO)_3NO]$ and 125 g of methanol, and thereafter 126 g (1 mole) of benzyl chloride were added under a carbon monoxide pressure of 1.7 bars at 45° C., with vigorous stirring. After two hours, the reaction mixture was acidified with hydrochloric acid and then extracted with ether. After conventional working up, the yield of phenylacetic acid was 78%. In addition, 11% of methyl phenylacetate were formed.

EXAMPLE 3

126 g (1 mole) of benzyl chloride were added in the course of 1.5 hours, with vigorous stirring, to a mixture of 9.5 g (0.05 mole) of the complex $Na[Fe(CO)_3NO]$, 90 g (1.2 moles) of calcium hydroxide, 320 g of methanol and 80 g of water, under a carbon monoxide pressure of 1.7 bars, at from 25° to 28° C.; the mixture was then heated at 55° C. for 4 hours, after which it was heated to the boil with 200 ml of concentrated hydrochloric acid for one hour. Working up by extraction with pentane gave methyl phenylacetate in 86% yield.

EXAMPLES 4–10

The following were prepared by the method described in Example 3 (in the case of the free acids, without esterification by means of hydrochloric acid):

4. 4-n-Butylphenylacetic acid (boiling point 90°–92° C./0.5 mm Hg), in 75% yield, from 4-n-butylbenzyl chloride.
5. Methyl 2-methylphenylacetate (boiling point 110° C./10 mm Hg), in 94% yield, from 2-methylbenzyl chloride.
6. Methyl 2-methyl-4-chlorophenylacetate (boiling point 90° C./0.5 mm Hg), in 62% yield, from 2-methyl-4-chlorobenzyl chloride.
7. Methyl 2-naphthylacetate (boiling point 120°–123° C./1 mm Hg), in 71% yield, from 2-chloromethylnaphthalene.
8. Dimethyl 1,2-phenylenediacetate (boiling point 120°–123° C./1 mm Hg), in 25% yield, from 1,2-xylylene dichloride.
9. Methyl 4-N-pyridylacetate (boiling point 123° C./15 mm Hg), in 25% yield, from 4-chloromethylpyridine.
10. Propyl phenylacetate, in 81% yield, from benzyl chloride and propanol (in place of methanol).

We claim:

1. In a process for the manufacture of arylacetic acids, and their esters, of the formula I $$Ar(CH_2-COOR)_n \quad I$$

where Ar is aryl, R is hydrogen or a hydrocarbon radical, and n is 1 or 2, by carbonylation of halomethylaryl compounds of the formula II $$Ar(CH_2X)_n \quad II$$

where X is chlorine, bromine or iodine, with carbon monoxide and an iron carbonyl compound as the catalyst and with stoichiometric amounts of an inorganic base or of an alcoholate of an alcohol ROH at a temperature of from about 20° to 120° C. and under a carbon monoxide pressure of from about 1 to 100 bars, the improvement which comprises using as said iron carbonyl compound a compound of the formula III $$M^+[Fe(CO)_3NO]^- \quad III$$

where M is an alkali metal cation or ammonium cation or one equivalent of an alkaline earth metal cation.

2. A process as set forth in claim 1 wherein M is sodium, potassium, ammonium, calcium or magnesium.

3. A process as set forth in claim 1 wherein M is sodium.

4. A process as set forth in claim 1 wherein from about 0.001 to 1 mole of III is available per mole of II.

5. A process as set forth in claim 1 wherein from about 0.02 to 0.2 mole of III is available per mole of II.

6. A process as set forth in claim 1, wherein Ar is

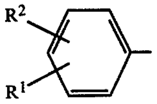

where $R^1$ is alkyl of 1 to 12 carbon atoms, vinyl, alkoxy of 1 to 4 carbon atoms, chlorine, phenyl or cyano, and $R^2$ is hydrogen or one of the meanings of $R^1$.

7. A process as set forth in claim 6, wherein X is Cl and n is 1.

8. A process as set forth in claim 1, wherein R is alkyl or alkenyl of up to 18 carbon atoms and n is 1.

9. A process as set forth in claim 1, wherein Ar is phenyl, R is H and n is 1.

10. A process as set forth in claim 1, wherein Ar is phenyl, R is methyl and n is 1.

11. A process as set forth in claim 1, wherein Ar is phenyl, R is alkyl or alkenyl of up to 18 carbon atoms, and n is 1.

* * * * *

UNITED STATES PATENT AND TRADEMARK OFFICE

CERTIFICATE OF CORRECTION

PATENT NO. : 4,424,394

DATED : January 3, 1984

INVENTOR(S) : Kurt SCHNEIDER et al.

It is certified that error appears in the above-identified patent and that said Letters Patent is hereby corrected as shown below:

On the title page in the abstract

Line 6, change it to read:

$M^+[Fe(O)_3NO]^-$ and not $m^+[Fe(O)_3NO]^-$

Signed and Sealed this

*Thirty-first* Day of *July 1984*

[SEAL]

*Attest:*

GERALD J. MOSSINGHOFF

*Attesting Officer* *Commissioner of Patents and Trademarks*